United States Patent [19]
Urakami et al.

[11] Patent Number: 5,774,223
[45] Date of Patent: Jun. 30, 1998

[54] OPTICAL MEASURING METHOD AND AN OPTICAL MEASURING APPARATUS FOR DETERMINING THE INTERNAL STRUCTURE OF AN OBJECT

[75] Inventors: Tsuneyuki Urakami; Mitsuharu Miwa; Yutaka Yamashita; Yutaka Tsuchiya, all of Hamamatsu, Japan

[73] Assignee: Hamamatsu Photonics K.K., Shiuoka-ken, Japan

[21] Appl. No.: 703,766

[22] Filed: Aug. 27, 1996

[30] Foreign Application Priority Data

Aug. 28, 1995 [JP] Japan ................................. 7-218510

[51] Int. Cl.[6] .......................... G01B 11/00; G01M 33/48
[52] U.S. Cl. ............................................. 356/394; 356/39
[58] Field of Search ............................... 356/394, 39, 41, 356/432, 442, 341, 5, 4, 40, 427, 121, 433, 337, 338; 364/480, 481, 486, 569, 579; 250/226, 339, 573, 574, 343, 564, 565

[56] References Cited

U.S. PATENT DOCUMENTS

| | | | |
|---|---|---|---|
| 3,952,206 | 4/1976 | Liedholz | 250/565 |
| 4,352,557 | 10/1982 | Schmid-Schonbein et al. | 356/39 |
| 5,153,664 | 10/1992 | Besesty et al. | 356/5 |
| 5,179,288 | 1/1993 | Miffitt et al. | 250/564 |
| 5,239,185 | 8/1993 | Ito et al. | 250/573 |
| 5,278,627 | 1/1994 | Aoyagi et al. | 356/41 |
| 5,499,190 | 3/1996 | Takahashi et al. | 364/481 |
| 5,529,065 | 6/1996 | Tsuchiya | 128/633 |
| 5,568,460 | 10/1996 | Saikan et al. | 369/100 |

FOREIGN PATENT DOCUMENTS

| | | |
|---|---|---|
| 0 252 578 | 1/1988 | European Pat. Off. . |
| 0 329 297 | 8/1989 | European Pat. Off. . |

OTHER PUBLICATIONS

Optics Letters/vol. 19, No. 24/Dec. 15, 1994, Possible Correlation Between Blood Glucose Concentration and the Reduced Scattering Coefficient of Tissues in the Near Infrared, J.S.Maier et al, pp. 2062–2064.

Phys.Med.Biol.1992, vol.37,No.7,1531–1560, Printed in the UK,The Theoretical Basis for the Determination of Optical Pathlengths in Tissue: Temporal and Frequency Analysis, S R Arridget et al, pp. 1531–1560.

Time Resolved Reflectance and Transmittance for the Non--Invasive Measurement of Tissue Optical Properties,M.S-.Patterson et al, 15 Jun. 1989/vol. 28,No.12/Applied Optics.pp. 2331–2336.

Technical Digest 1996 Biomedical Optical Spectroscopy and Diagnostics, Mar. 20–22, 1996 Orlando, Florida, pp. 93–94.

Analytical biochemistry 195, 330–351 (1991) Quantitation of Time–and Frequency–Resolved Optical Spectra for the Determination of Tissue Oxygenation,E.M.Sevick et al. pp. 330–351.

*Primary Examiner*—Frank G. Font
*Assistant Examiner*—Michael P. Stafira
*Attorney, Agent, or Firm*—Cushman, Darby & Cushman IP Group of Pillsbury, Madison & Sutro LLP

[57] ABSTRACT

An optical measuring method and an optical measuring apparatus are capable of obtaining the true mean time delay of a light waveform within a short time for the purpose of obtaining information on the internal structure of an object. Calculations include a first mean time delay when the light path includes the object, a second mean time delay when the light path does not include the object, and a subtraction of the second mean time delay from the first mean time delay to obtain a true mean time delay.

18 Claims, 6 Drawing Sheets

OPTICAL MEASURING METHOD AND AN OPTICAL MEASURING APPARATUS FOR DETERMINING THE INTERNAL STRUCTURE OF AN OBJECT

BACKGROUND OF THE INVENTION

1. Field of the Invention

The present invention relates to the technology for optically measuring an object, and more particularly, to the technology for measuring internal information of a scattering medium.

2. Related Background Art

If we were able to obtain in vivo information without cutting an organism open, it would be fairly magnificent in terms of cure and prevention of disease. For example, in the case of the Alzheimer disease, which is a cause of dementia, a phenomenon of atrophy of brain is observed, and in the case of cancer, tissue different from the normal tissue appears. Thus, knowledge of in vivo structure can supply very useful information to prevention and cure of these diseases. Also in such cases, very easy diagnosis would be possible, if the in vivo information were able to be obtained without cutting the organism open. Further, demand is also great for always monitoring the vital information without giving a patient pain in performing surgery or in capturing a condition of the disease of an inpatient.

In view of such demand, currently widely used methods include those for measuring the in vivo information using the X-rays, magnetic field, or positron. The X-rays are often used in the medical equipment for roentgenography or X-ray CT (computed tomography) because of their transmission characteristics through the organism and straight advance property. The magnetic field is often used in CT by the technique of MRI. Positron is used in CT performed as injecting a medicine containing a radioactive isotope into the organism and detecting γ-rays radiated when the isotope decays.

However, recently there is an increasing demand to acquire the in vivo information using the light existing anywhere in the natural world, especially, using the light ranging from the near infrared region to the visible region.

Since the organism is a scattering medium, measuring the organism is nothing but measuring the scattering medium. A generally known example of the techniques studied in the technical field concerning the measurement of a scattering medium is a method of letting a light pulse, which can be regarded almost as a delta function in terms of the time, enter the scattering medium and analyzing a waveform of light transmitted or reflected by the scattering medium. There are various approaches to analyzing the waveform of light, one of which is a method for obtaining the center of gravity (mean time delay) of the waveform.

In this method, an evaluation is made of the mean time delay (center of gravity) of a so-called impulse response, and, for obtaining the impulse response, it is necessary to use a photodetector and light source such that the time resolution of the photodetector and the pulse width of incident light may be sufficiently narrow so as to be ignorable relative to the impulse response of an object evaluated. Such a light source itself either does not exist, depending upon the wavelength or light power necessary, or does exist and is very expensive or often difficult to control. Similarly, such a photodetector cannot detect the light, depending upon the wavelength of light to be detected or the light quantity, or can detect the light but is expensive.

Then, a generally used technique is a technique known as deconvolution which uses a light pulse that cannot be regarded as a delta function, or a photodetector with a response characteristic that cannot be regraded as a delta function, thereby eliminating influence of the spread of the light waveform of the light source and the response of photodetector, i.e., eliminating influence of an instrumental function.

Deconvolution is a technique for obtaining a true waveform by an inverse arithmetic computation when an observation result is expressed by a convolution of the true waveform and the instrumental function. This will be explained specifically.

Let i(t) be the true waveform, o(t) be an observed waveform, and h(t) be the instrumental function. Then the relation among them is expressed by the following Equation 1.

$$o(t) = \int_{-\infty}^{\infty} h(t-t')i(t')dt' = h(t)*i(t)$$

In the equation, * represents the convolution.

For attaining the mean time delay of the true waveform, the conventional approaches were to perform an arithmetic computation to obtain the mean time delay of the true waveform after performing the inverse arithmetic computation of the above equation, namely, obtaining the true light waveform i(t) by deconvolution processing.

Various algorithms are known as an arithmetic computation for deconvolution in the above technique, but any one of the algorithms, when employed, requires a long period of time for obtaining a calculation result of the mean time delay because of a long arithmetic period. This raised the problem that, in the case where data is repetitively acquired in order to monitor temporal change of a state of the measured object, it was difficult in terms of the time to obtain an accurate measurement result by increasing the number of repetitions.

When in the above method the measurement is carried out using a measuring system with an instrumental function that is nearly zero, it is necessary to perform the measurement with very high time resolution, which brings a disadvantage in that the apparatus becomes expensive.

SUMMARY OF THE INVENTION

The present invention has been developed to solve the above problems. An object of the invention is to provide an optical measuring method and an optical measuring apparatus capable of obtaining the true mean time delay of a light waveform within a short time so as to obtain the internal information of a measured object.

An optical measuring method of the present invention comprises:

a first step of, in a first state in which a measured object is placed in a predetermined place, emitting probe light from a light source onto the measured object and detecting the probe light transmitted or reflected by said measured object by means of light detecting means to obtain a first mean time delay of said probe light;

a second step of, in a second state in which the measured object is not placed in said predetermined place, emitting the probe light from said light source to the predetermined place and detecting the probe light passing through said predetermined place without intervention of said measured object by said light detecting means to obtain a second mean time delay; and a third step of subtracting said second mean time delay from said first mean time delay to obtain a true mean time delay.

The optical measuring method of the present invention preferably further comprises a fourth step of analyzing said true mean time delay obtained in the third step to obtain internal information of said measured object.

Further, the optical measuring method of the present invention may further comprise:

a fifth step of, in the first state in which the measured object is placed in said predetermined place, emitting the probe light from the light source to the measured object and detecting the probe light transmitted or reflected by said measured object by the light detecting means to obtain a first integral value of a waveform of said probe light; a sixth step of, in the second state in which the measured object is not placed in said predetermined place, emitting the probe light from said light source to said predetermined place and detecting the probe light passing said predetermined place without intervention of the measured object by said light detecting means to obtain a second integral value of a waveform of the probe light; and a seventh step of obtaining a ratio of said first integral value and said second integral value. In this case, the method can further comprise an eighth step of analyzing the true mean time delay obtained in said third step and the ratio of the first integral value and the second integral value obtained in said seventh step to obtain internal information of said measured object.

An optical measuring apparatus of the present invention comprises:

(a) a light source for emitting probe light to be guided to a predetermined place;

(b) light detecting means for detecting the probe light output from said predetermined place; and (c) a first arithmetic processing portion for calculating a first mean time delay of the probe light transmitted or reflected by a measured object, based on the probe light detected by said light detecting means in a first state in which the measured object is placed in said predetermined place, calculating a second mean time delay of the probe light passing through said predetermined place without intervention of said measured object, based on the probe light detected by said light detecting means in a second state in which the measured object is not placed in said predetermined place, and subtracting the second mean time delay from the first mean time delay to obtain a true mean time delay.

The first arithmetic processing portion may comprise a mean time delay arithmetic unit for calculating a mean time delay of the probe light detected by said light detecting means to obtain said first mean time delay and said second mean time delay, and a difference arithmetic unit for subtracting said second mean time delay from said first mean time delay to obtain the true mean time delay. A preferred example of said difference arithmetic unit comprises first switching means for switching a destination of output data from said mean time delay arithmetic unit, first memory means connected to said first switching means and arranged to memorize said second mean time delay, and difference arithmetic means connected to said first switching means and to said first memory means and arranged to subtract the second mean time delay stored in said first memory means from said first mean time delay to obtain the true mean time delay.

Also, the optical measuring apparatus of the present invention may further comprise:

(d) first light waveguide means, one end of which is connected to said light source and the other end of which is disposed to face said predetermined place, for guiding said probe light to said predetermined place; and (e) second light waveguide means, one end of which is connected to said light detecting means and the other end of which is disposed to face said predetermined place, for guiding the probe light output from said predetermined place to said light detecting means.

Further, the optical measuring apparatus of the present invention preferably further comprises (f) an analyzing unit for analyzing the true mean time delay obtained by said first arithmetic processing portion to obtain the internal information of said measured object.

The optical measuring apparatus of the present invention may further comprise (g) a second arithmetic processing portion for calculating a first integral value of a waveform of the probe light transmitted or reflected by said measured object, based on the probe light detected by said light detecting means in the first state in which the measured object is placed in said predetermined place, calculating a second integral value of a waveform of the probe light passing through said predetermined place without intervention of the measured object, based on the probe light detected by said light detecting means in the second state in which the measured object is not placed in said predetermined place, and obtaining a ratio of said first integral value and said second integral value. In this case, said analyzing unit can analyze the true mean time delay obtained by said first arithmetic processing portion and the ratio of the first integral value and the second integral value obtained by said second arithmetic processing portion to obtain the internal information of said measured object.

The second arithmetic processing portion may comprise an integration arithmetic unit for calculating an integral value of a waveform of the probe light detected by said light detecting means to obtain said first integral value and said second integral value, and a ratio arithmetic unit for obtaining the ratio of said first integral value and said second integral value. A preferred example of said ratio arithmetic unit comprises second switching means for switching a destination of output data from said integration arithmetic unit, second memory means connected to said second switching means and arranged to store said second integral value, and ratio arithmetic means connected to said second switching means and to said second memory means and arranged to obtain the ratio of said first integral value and the second integral value stored in said second memory means.

A scattering medium can be employed as the foregoing measured object. In this case, the internal information can be at least one information selected from the group consisting of the constant concerning absorption of the scattering medium, the constant concerning scattering thereof, the refractive index thereof, the degree of heterogeneity of composition thereof, and the constant concerning the structure thereof.

According to the knowledge of the inventors, when the arithmetic operation is carried out to subtract the second mean time delay (i.e., the center of gravity of the instrumental function) of the probe light detected by the light detecting means without intervention of the measured object from the first mean time delay (i.e., the center of gravity of the observed waveform) of the probe light transmitted or reflected by the measured object, the true mean time delay (the true center of gravity of the waveform of the probe light) can be obtained that is removing the influence effected on the light waveform by the spread of the probe light waveform due to the characteristics of the light source and the response characteristics of the light detecting means, effectively removes the influence of the instrumental function.

The optical measuring method of the present invention is arranged to perform the above subtraction to quickly and easily attain the true mean time delay. Since the light transmitted or reflected by the measured object contains the internal information of the measured object, the internal information of measured object (for example, the constant of the scattering medium as to absorption or scattering, the refractive index thereof, the degree of heterogeneity of composition, or the constant concerning the structure) can be acquired by analyzing the data of the true mean time delay thus obtained. Therefore, the optical measuring method of the present invention permits us to accurately gain the in vivo information without cutting the organism open, thus permitting inspection or diagnosis of disease.

When the optical measuring method of the present invention is arranged to obtain the ratio of the first integral value of the waveform of the probe light transmitted or reflected by the measured object and the second integral value of the waveform of the probe light detected by the light detecting means without intervention of the measured object, the internal information of the measured object can be obtained in more detail by analyzing the data of this ratio and the true mean time delay.

In the optical measuring apparatus of the present invention, the first arithmetic processing portion is arranged to calculate the first mean time delay, i.e., the center of gravity of the measured waveform and the second mean time delay, i.e., the center of gravity of the instrumental function and then to subtract the second mean time delay from the first mean time delay to obtain the true mean time delay, whereby the true mean time delay of the probe light can be quickly and easily obtained by removing the influence effected on the light waveform by the spread of the probe light waveform due to the characteristics of the light source and the response characteristics of the light detecting means.

When the first arithmetic processing portion comprises the mean time delay arithmetic unit and the difference arithmetic unit, the mean time delay arithmetic unit calculates each of the first and second mean time delays and then supplies each mean time delay data to the difference arithmetic unit. The difference arithmetic unit executes the arithmetic operation to subtract the second mean time delay from the first mean time delay, based on the mean time delay data, so as to obtain the true mean time delay. Particularly, when the difference arithmetic unit comprises the first switching means, the first memory means, and the difference arithmetic means, the second mean time delay data from the mean time delay arithmetic unit is input through the first switching means into the first memory means, and is stored therein. On the other hand, the first mean time delay data from the mean time delay arithmetic unit is input through the first switching means into the difference arithmetic means. The difference arithmetic means reads the second mean time delay data out of the first memory means in accordance with the input of the first mean time delay and executes the arithmetic operation to subtract the second mean time delay from the first mean time delay so as to obtain the true mean time delay.

With the apparatus provided with the first and second light waveguide means among the optical measuring apparatus of the present invention, the first light waveguide means can easily and surely guide the probe light from the light source to the measured object and the second light waveguide means can surely guide the probe light transmitted or reflected by the measured object to the light detecting means. With the apparatus arranged to comprise the analyzing portion and to measure the scattering medium as a measured object among the optical measuring apparatus of the present invention, the true mean time delay data output from the first arithmetic processing portion is supplied to the analyzing unit. The analyzing unit executes the analysis based on the true mean time delay data to obtain the desired internal information of the scattering medium, for example, the constant concerning absorption or scattering of the scattering medium, the refractive index thereof, the degree of heterogeneity of composition, or the constant concerning the structure. Therefore, the optical measuring apparatus can accurately acquire the in vivo information without cutting the organism open, thus permitting inspection or diagnosis of disease.

With the apparatus comprising the second arithmetic processing portion among the optical measuring apparatus of the present invention, the second arithmetic processing portion obtains the ratio of the first integral value and the second integral value and the analyzing unit analyzes the ratio arithmetic data and the true mean time delay data, thereby obtaining the more detailed internal information of the measured object.

When the second arithmetic processing portion comprises the integration arithmetic unit and the ratio arithmetic unit, the integration arithmetic unit calculates each of the first and second integral values and supplies each integral data to the ratio arithmetic unit. The ratio arithmetic unit executes the arithmetic operation (i.e., the ratio arithmetic) to obtain the ratio of the first integral value and the second integral value, based on the integral data supplied. Particularly, when the ratio arithmetic unit comprises the second switching means, the second memory means, and the ratio arithmetic means, the second integral data from the integration arithmetic unit is supplied through the second switching means to the second memory means, and is stored therein. On the other hand, the first integral data from the integration arithmetic unit is input through the second switching means to the ratio arithmetic means. The ratio arithmetic means reads the second integral data out of the second memory means in accordance with the input of the first integral data and then executes the arithmetic operation to obtain the ratio of the first integral value and the second integral value.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The embodiments of the present invention will be explained in detail with reference to the accompanying drawings. In the description with the drawings, same elements will be denoted by same reference numerals, and redundant description will be omitted.

Figure 1A:
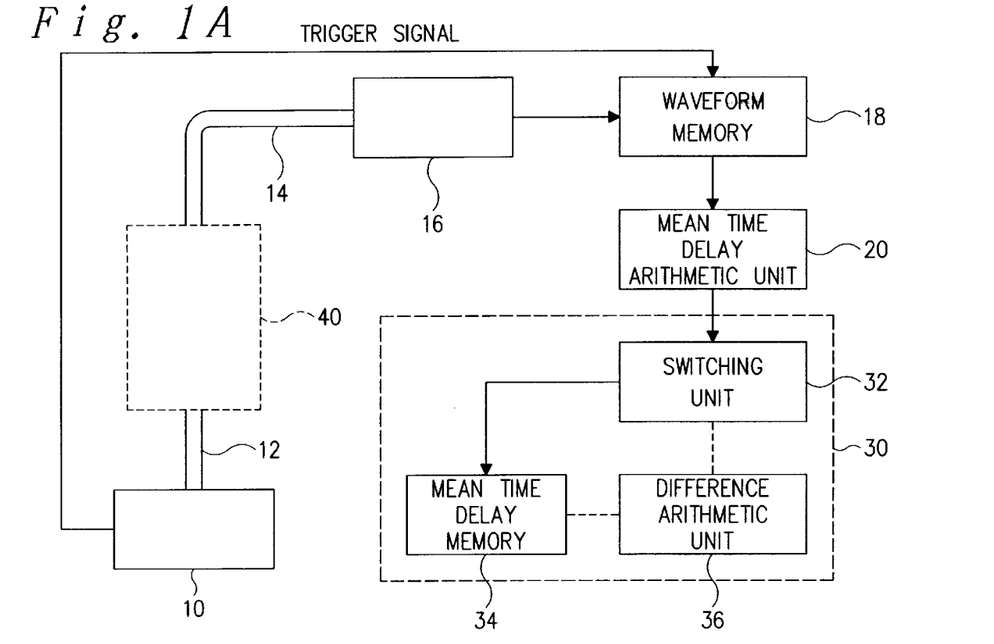
FIG. 1A and FIG. 1B are block diagrams to show an example of the optical measuring apparatus of the present invention in the second state and in the first state, respectively.
Figure 1B:
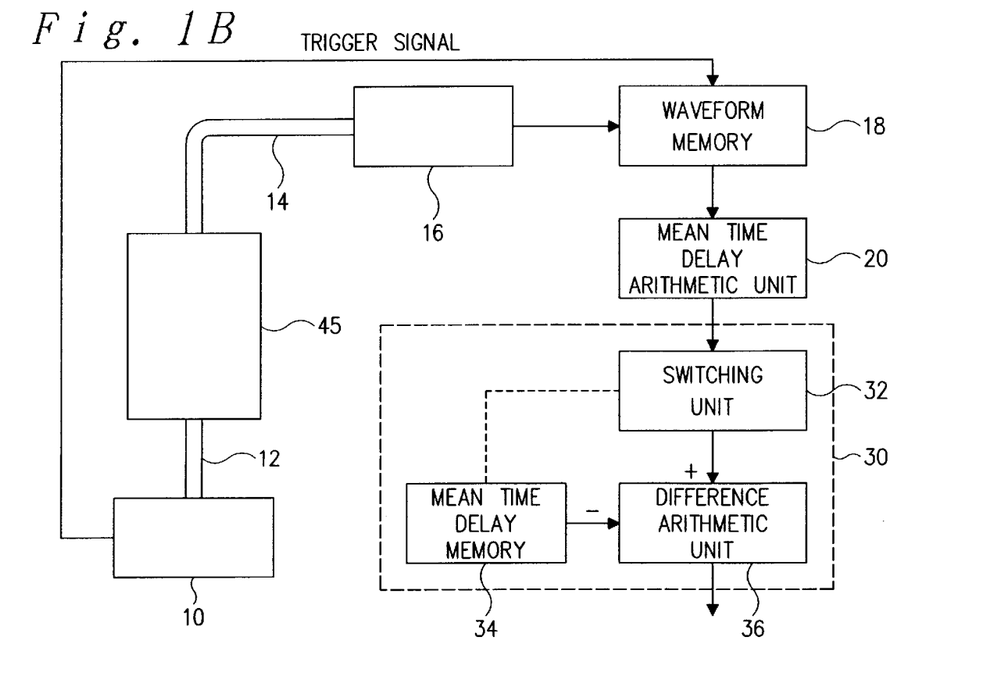

FIG. 1A and FIG. 1B are block diagrams each to show the structure and operation of the optical measuring apparatus of the present embodiment. The optical measuring apparatus of the present embodiment is provided with a light source 10, light waveguide means 12 and 14 such as optical fibers, a photodetector 16, a waveform memory 18, a mean time delay arithmetic unit 20, and a difference arithmetic section 30.

The light source 10 emits short pulsed light, which is the probe light. The light source 10 is connected to one end of the light waveguide means 12, so that the probe light emitted from the light source 10 is incident thereto. One end of the light waveguide means 14 is disposed to face the other end of the light waveguide means 12 with a region (predetermined portion) 40 between them, so that the probe light having emerged from the light waveguide means 12 and having passed through the region 40 is incident to the one end of the light waveguide means 14. An object to be measured is positioned in the region 40 upon inspection, as shown in FIG. 1B.

The photodetector 16 is connected to the other end of the light waveguide means 14. This photodetector 16 receives the probe light having traveled in the light waveguide means 14 and outputs an electric signal according to the intensity of the light. The waveform memory 18 is connected to the photodetector 16 and stores data of light waveform indicated by the output signal from the photodetector 16. A trigger signal is supplied from the light source 10 to the waveform memory 18, and the waveform memory 18 is arranged to take in the light waveform data from the photodetector 16 in synchronization with emission of the probe light.

The mean time delay arithmetic unit (gravity center arithmetic unit) 20 is connected to the waveform memory 18. The mean time delay arithmetic unit 20 calculates the mean time delay (the center of gravity of light waveform) of the light detected by the photodetector 16, based on the data stored in the waveform memory 18.

The difference arithmetic section 30 is connected to the mean time delay arithmetic unit 20. This difference arithmetic section 30 is comprised of a switching unit 32, a memory 34, and a difference arithmetic unit 36. The switching unit 32 is connected to the mean time delay arithmetic unit 20, and the mean time delay memory (gravity center memory) 34 and difference arithmetic unit 36 each are connected to the switching unit 32. The switching unit 32 is arranged to switch a destination of output data from the mean time delay arithmetic unit 20 between the mean time delay memory 34 and the difference arithmetic unit 36. The mean time delay memory 34 stores the output data from the mean time delay arithmetic unit 20. The difference arithmetic unit 36 subtracts the data stored in the mean time delay memory 34 from the data input from the mean time delay arithmetic unit 20 through the switching unit 32.

Next explained are the operation of the optical measuring apparatus of the present embodiment and the optical measuring method of the present embodiment. First, as shown in FIG. 1A, the light source 10 emits the probe light in a state in which no measured object is placed in the region 40 (or in the second state). The probe light advances in the light waveguide means 12 to be emitted to the region 40. The probe light travels through the region 40 to enter the light waveguide means 14 and to be guided to the photodetector 16 by the light waveguide means 14. This results in the photodetector 16 detecting a temporal waveform of the probe light having passed through the region 40. This light waveform data is taken into the waveform memory 18 at a timing synchronized with the probe light and is stored therein.

The mean time delay arithmetic unit 20 reads the light waveform data out of the waveform memory 18 as occasion demands, and it performs a predetermined arithmetic based on the data to calculate the mean time delay of the probe light. This mean time delay is the mean time delay H of the instrumental function $$h(t) \left( = \int_{-\infty}^{+\infty} t \cdot h(t) dt / \int_{-\infty}^{+\infty} h(t) dt \right).$$

Examples of the instrumental function h(t) conceivably include the pulse waveform of the probe light, the response function of the photodetector 16, other signal distortion caused by signal lines for transmitting the electric signal, and so on.

The mean time delay data of the instrumental function h(t) thus obtained is input into the switching unit 32. The destination of the data controlled by the switching unit 32 is preliminarily set to be the mean time delay memory 34, and the mean time delay data of the instrumental function h(t) is thus input into the mean time delay memory 34. This results in the mean time delay data of h(t) being stored in the mean time delay memory 34.

Next, as shown in FIG. 1B, the light source 10 emits the probe light in a state in which the measured object 45 is placed in the region 40 (or in the first state). This probe light advances in the light waveguide means 12 to enter the measured object 45. The probe light having passed through the measured object 45 and having entered the light waveguide means 14 travels in the light waveguide means 14 to be received by the photodetector 16. The light waveform data detected by the photodetector 16 in this manner is one reflecting the internal information of the measured object 45. This light waveform data is stored in the waveform memory 18 and is used for the mean time delay arithmetic of the mean time delay arithmetic unit 20. The mean time delay calculated at this time by the mean time delay arithmetic unit 20 is the mean time delay of the observed waveform o(t). The mean time delay data of the observed waveform o(t) is input into the switching unit 32. The destination of the data controlled by the switching unit 32 is preliminarily set to be the difference arithmetic unit 36, so that the mean time delay data of the observed waveform o(t) is input into the difference arithmetic unit 36. The difference arithmetic unit 36 reads the mean time delay data of the instrumental function h(t) out of the mean time delay memory 34 and subtracts the mean time delay of the instrumental function h(t) from the mean time delay of the observed waveform o(t).

According to the knowledge of the inventors, the mean time delay of the true waveform i(t) can be obtained by subtracting the mean time delay of the instrumental function h(t) from the mean time delay of the observed waveform o(t). The principle thereof will be explained.

When the true waveform is i(t), the observed waveform o(t), and the instrumental function h(t), the relation among them is generally expressed by Eq. 2.

$$o(t) = \int_{-\infty}^{\infty} h(t-t')i(t')dt' = h(t)*i(t)$$

In the following, the integration domain ranges from $-\infty$ to $+\infty$ unless otherwise stated.

Letting I, O, and H be the mean time delays of i(t), o(t), and h(t), respectively, they are expressed as follows.

$$I = \int t \cdot i(t)dt / \int i(t)dt \quad (3)$$

$$O = \int t \cdot o(t)dt / \int o(t)dt \quad (4)$$

$$H = \int t \cdot h(t)dt / \int h(t)dt \quad (5)$$

Let us calculate the numerator and the denominator of O. First calculated is the numerator of O.

$$\begin{aligned}\int t \cdot o(t)dt &= \int t \cdot \{\int h(t-t')i(t')dt'\}dt \\ &= \iint t \cdot h(t-t')i(t')dt'dt \\ &= \int i(t')dt' \int t \cdot h(t-t')dt\end{aligned}$$

Here, putting $t-t'=\tau$, $t=\tau+t'$ and $dt = d\tau$. Then, $$\begin{aligned}\int t \cdot o(t)dt &= \int i(t')dt' \int (\tau+t') \cdot h(\tau)d\tau \\ &= \int i(t')dt' \int \{\tau \cdot h(\tau) + t' \cdot h(\tau)\}d\tau \\ &= \int i(t')dt' \int \tau \cdot h(\tau)d\tau + \int t' \cdot i(t')dt' \int h(\tau)d\tau\end{aligned} \quad (6)$$

Next, the denominator of O is calculated.

$$\begin{aligned}\int o(t)dt &= \iint h(t-t')i(t')dt'dt \\ &= \int i(t')dt' \int h(t-t')dt\end{aligned}$$

Here, putting $t-t'=\tau$, $t=\tau+t'$ and $dt=d\tau$. Then,

From (6) and (7),

From (6) and (7), $$\begin{aligned}O &= \{\int i(t')dt' \int \tau \cdot h(\tau)d\tau + \\ &\quad \int t' \cdot i(t')dt' \int h(\tau)d\tau\} / \int i(t')dt' \int h(\tau)d\tau \\ &= \int \tau \cdot h(\tau)d\tau / \int h(\tau)d\tau + \int t' \cdot i(t')dt' / \int i(t')dt' \\ &= H + I\end{aligned} \quad (8)$$

The foregoing proved that the mean time delay O of the observed waveform o(t) is expressed by a sum of the mean time delay H of the instrumental function h(t) and the mean time delay I of the true waveform i(t).

As apparent from the foregoing, the mean time delay I of the true waveform i(t) is obtained by subtracting the mean time delay H of the instrumental function h(t) from the mean time delay O of the observed waveform o(t). The difference arithmetic unit 36 is one for executing this arithmetic, and thus, the output data from the difference arithmetic unit 36 is the mean time delay data of the true waveform i(t). Therefore, the true mean time delay is attained for the waveform of the probe light, useful in acquiring the internal information of the measured object.

Since the optical measuring apparatus of the present embodiment can obtain the true mean time delay of the probe light waveform by such simple processing as to subtract the mean time delay of the instrumental function preliminarily obtained from the mean time delay of the observed waveform of the probe light, as explained above, it can obtain the true mean time delay of the probe light waveform more quickly than by the techniques using the conventional deconvolution processing.

Specific examples of the above photodetector 16 include a phototube (PT), a photomultiplier tube (PMT), a photomultiplier tube (MCP-PMT) incorporating a multichannel plate (MCP), a photodiode (PD), an avalanche photodiode (APD), and so on. The above photodetector is usually one for converting a light waveform into an electric waveform on an analog basis, but the photodetector can also perform digital measurement of waveform when used in the photon count region. In this case, the photodetector generates an electric pulse signal corresponding to a photon. The electric signal is amplified to the amplitude processable by a subsequent electronic circuit, and thereafter a detection time distribution of electric pulse signal is obtained as counting signals with the detection time on the abscissa. In this case a reference signal of the time (hereinafter referred to as "start signal") employed is a synchronizing signal obtained from an electric signal used for generating the probe light pulse or an electric signal synchronized with the light pulse obtained when the photodetector detects the probe pulse. The start signal and the electric signal obtained by photon detection (hereinafter referred to as "stop signal") are input into a time-amplitude converter (hereinafter referred to as "TAC"). The TAC converts a time interval into an amplitude of output signal and a light signal waveform can be obtained by analyzing it by a pulse height analyzer (PHA). In order to increase the resolution of detection time of photon, a constant fraction discriminator (hereinafter referred to as "CFD") is effective when set before TAC. The waveform memory can store the output signal intensity distribution obtained by the above measurement in the form of a time distribution.

The apparatus of the present embodiment is arranged to input the trigger signal from the light source 10 into the waveform memory 18, but the apparatus may be modified to input the trigger signal into the processing system after the waveform memory 18. In this case, the mean time delay of the probe light is obtained by performing the arithmetic processing as properly delaying the time component of the light waveform in accordance with input of the trigger signal.

Further, the apparatus of the present embodiment is arranged to detect the probe light transmitted by the measured object 45, but the apparatus may be modified to detect the probe light reflected by the measured object 45. In this case, for example, a light waveguide means other than the light waveguide means 12 and 14 is located at a position of incidence of the probe light reflected by the measured object 45, and this light waveguide means is connected to the photodetector 16.

The above embodiment is arranged to obtain the second mean time delay in the second state in which the measured object is not placed in the predetermined portion and thereafter to obtain the first mean time delay in the first state in which the measured object is placed in the predetermined portion, but the apparatus may be modified to perform the operation in the reverse order.

Various internal information of the measured object can be acquired using the true mean time delay data of the probe light obtained by the optical measuring apparatus of the present embodiment. Next explained is the apparatus for measuring the internal information of scattering medium, arranged to include the optical measuring apparatus of the present embodiment.

Figure 2:
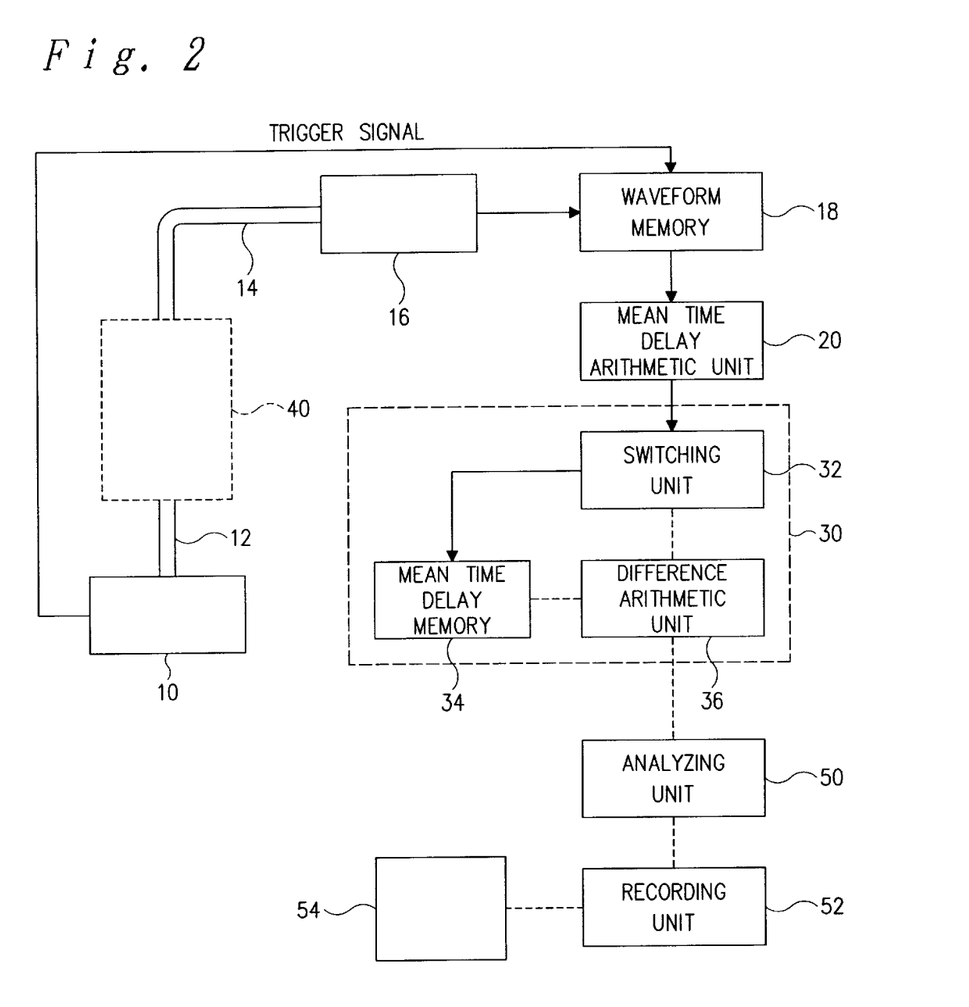
FIG. 2 is a block diagram to show an example of the optical measuring apparatus for measuring the internal information of scattering medium according to the present invention in the second state.
Figure 3:
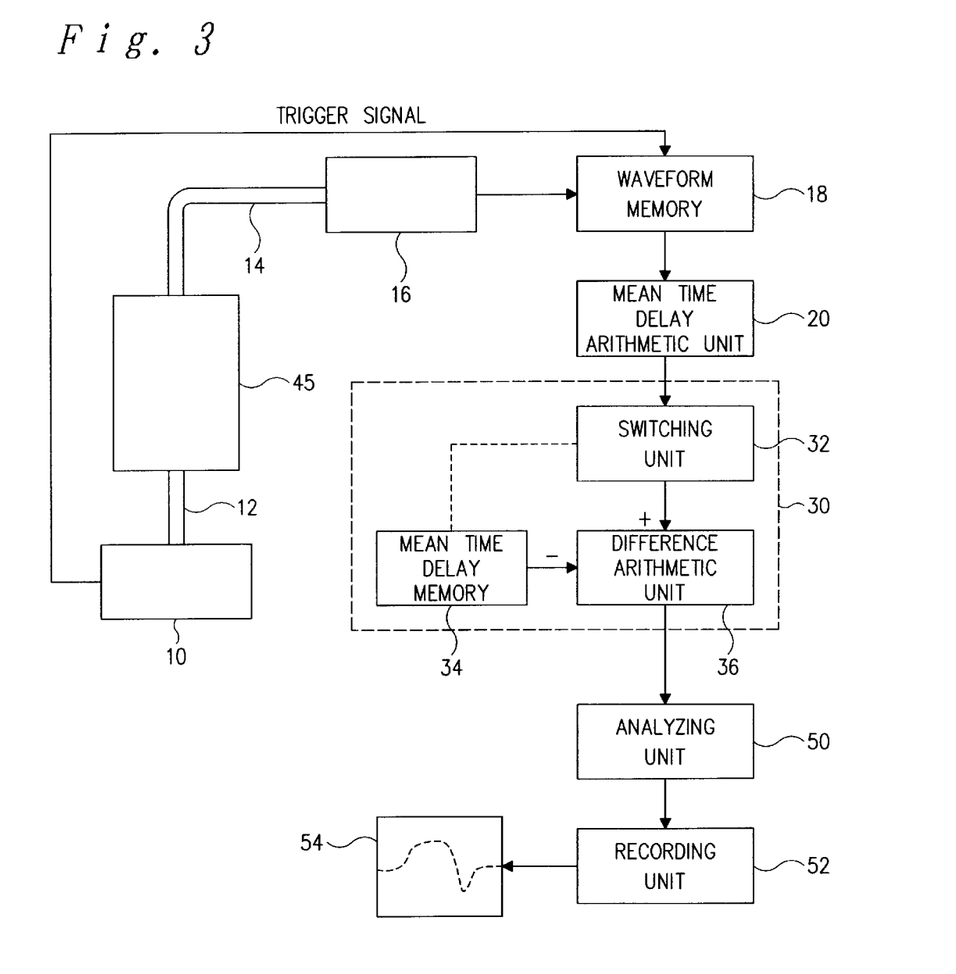
FIG. 3 is a block diagram to show the example of the optical measuring apparatus for measuring the internal information of scattering medium according to the present invention in the first state.

FIG. 2 and FIG. 3 are block diagrams to show the structure and operation of such an optical measuring apparatus. This apparatus is provided with the optical measuring apparatus (FIG. 1A and FIG. 1B) explained above, an analyzing unit 50 connected to the difference arithmetic unit 36, a recording unit 52 connected to the analyzing unit 50, and a displaying unit 54 connected to the recording unit 52.

The analyzing unit 50 executes a predetermined arithmetic based on the true mean time delay data output from the difference arithmetic unit 36 to obtain predetermined internal information of the scattering medium 45. The recording unit 52 records the internal information data obtained by the analyzing unit 50 and stores it. The displaying unit 54 displays a graph of the internal information data obtained by the analyzing unit 50 on a screen. Provision of the recording unit 52 and displaying unit 54 makes it easy to track a temporal change of the internal state of the scattering medium 45.

The content of the arithmetic processing of the analyzing unit 50 differs depending upon the type of the internal information of the scattering medium 45 to be obtained. For example, when an absorption coefficient $\mu_a$ is obtained from the mean time delay obtained by the difference arithmetic unit 36, the analyzing unit 50 performs an arithmetic based on a theoretical formula expressing an impulse response with a parameter of absorption coefficient $\mu_a$. The solution to the photon diffusion equation often used as such a theoretical formula, i.e., a waveform of the output light measured when pulsed light with sufficiently short pulse width is incident to the measured object, is given as follows.

$$f(t)=(\pi c D)^{-3/2} t^{-5/2} \exp(-\mu_a c t)\exp\{-r^2/(4Dct)\}$$

Here,
- c: the velocity of photon in the medium
- D: the photon diffusion coefficient ($=1/(3\mu_s')$, where $\mu_s'$ is a transport scattering coefficient)
- $\mu_a$: the absorption coefficient
- t: the time
- r: a distance between the light source and the photodetector Letting c' be the velocity of photon in vacuum and n be a refractive index of measured object, c=c'n. Further, the above transport scattering coefficient $\mu_s'$ is defined as $\mu_s'=(1-g)\mu_s$, where g is a mean cosine of scattering angle of photon by the scattering medium.

This solution is obtained under a condition for infinitely large measured object. The form of the equation changes more or less depending upon the configuration of the scattering medium to be measured, the boundary condition, or the like, but in that case, the solution can also be obtained basically as a modification of the above formula or as an addition of some condition to the above formula.

The theoretical formula of mean time delay is attained by dividing an integral of f(t) weighted by t, ∫t.f(t)dt, by the integral of the above formula, ∫f(t)dt. There are various theoretical formulae, well known, depending upon the configuration of the scattering medium, which are described, for example, in the report by S. R. Arridge et al., "Theoretical Basis. for the Determination of Optical Pathlengths in Tissue: Temporal and Frequency Analysis" (Physics in Med. & Biol., DECEMBER, 1991).

Since the theoretical formula of mean time delay is a function of absorption coefficient $\mu_a$, the absorption coefficient $\mu_a$ can be conversely calculated using the mean time delay data obtained by the difference arithmetic unit 36. Similarly, the internal information such as the scattering constant, the refractive index, or the like of the scattering medium 45 can also be attained when the analyzing unit 50 executes converse calculation using the mean time delay data or an arithmetic to solve simultaneous equations. Therefore, desired internal information can be obtained by setting the arithmetic operation in the arithmetic unit 50, depending upon the type of the internal information.

An example of detecting a change in refractive index is measurement of blood glucose concentration. For example, as described in the report by John S. Maier et al., "Possible correlation between blood glucose concentration and the reduced scattering coefficient of tissues in the near infrared" (OPTICS LETTERS/Vol. 19, No. 24/Dec. 15, 1994), it is considered that the glucose concentration in tissue greatly affects the refractive index of extracellular fluid. Since the light scattering coefficient in the tissue largely depends upon the index difference between the extracellular fluid and cells, the index change of extracellular fluid changes the scattering coefficient so as to change the output waveform, appearing as a change of mean time delay. Since there is a correlation between the mean time delay of the light having passed through the scattering medium and the refractive index of extracellular fluid as described, the refractive index of extracellular fluid can be obtained by performing an appropriate arithmetic based on the mean time delay data in the analyzing unit 50.

It is general to use the photon diffusion equation as a formula for obtaining the internal information parameter such as the scattering constant or the absorption constant from the mean time delay data as described above, but the formula is not always limited to this. For example, examples applicable include a formula derived from an expression in which absorption of light inside the scattering medium is expressed as a function of propagation distance, a relational formula between the mean time delay and the internal information parameter obtained by experiments, and so on.

It is also possible to obtain the degree of heterogeneity of tissue of the scattering medium 45 or a constant concerning the structure thereof, using the mean time delay data. If a model can be established for the tissue of the scattering medium 45, the degree of heterogeneity of the tissue or the constant concerning the structure can be quantified by applying an appropriate formula to the model. Even in the case of application of model being not easy, a value of a parameter concerning the scattering medium 45 can be obtained by preliminarily investigating the correlation between the parameter and the mean time delay of waveform of the light transmitted or reflected by the scattering medium 45. In this case, the analyzing unit 50 performs a process to compare the mean time delay data from the difference arithmetic unit 36 with the predetermined correlation data to obtain the predetermined parameter.

Figure 4:
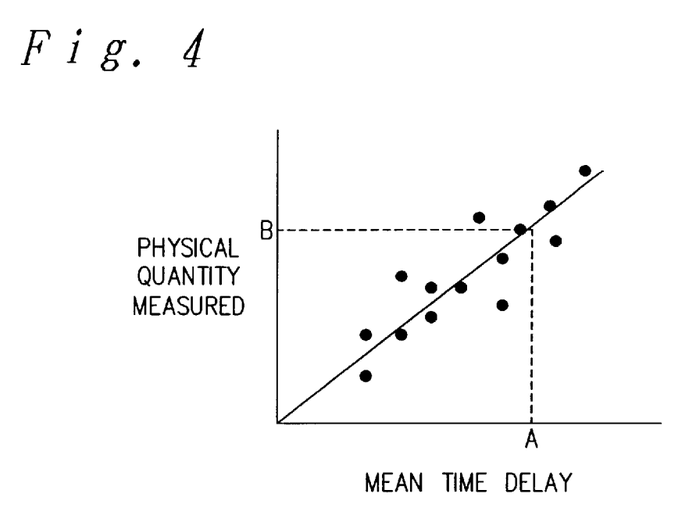
FIG. 4 is a graph to show an example of the correlation between the true mean time delay and the state of measured object.

Let us consider here an example in which the true mean time delay of the light measured has the correlation shown in FIG. 4 with a state of the measured object (for example, the composition or the structure). In FIG. 4, dots indicate data obtained by plural measurements actually performed for a human body, and the straight line indicates a correlation line obtained from the measured values. Supposing point A is a value of the mean time delay obtained for the human body of measured object, it is seen that the state of that person is approximately B, and a measuring person (for example, a doctor), checking it, can make a judgment about whether more detailed measurement (inspection) is necessary or not.

Since the merit of diagnosis with light is that the diagnosis can be made in a noninvasive manner, for example in the case of measurement of blood glucose concentration, the light is guided to a portion relatively easy to measure, such as a finger or an arm, and the transmitted light is detected at a point a predetermined distance therefrom. Upon that measurement, the light source and detector may be attached directly to the measured portion, or they may be arranged in such a manner that the light is guided from the light source to the human body by an optical fiber or the like and the light emerging from the human body is guided to the detector by an optical fiber or the like.

If a correlation is gained between the condition of disease or the condition of body and the mean time delay measured, useful information can be acquired directly from the mean time delay data. For example, if there is a correlation between a change of measured value and a structural change of tissue, a degree of the structural change can be obtained from the change of mean time delay, utilizing the correlation. If the arithmetic processing of the analyzing unit 50 is set to one for acquiring the information concerning the structural change of measured object, the optical measuring apparatus shown in FIG. 2 and FIG. 3 can be applied to diagnosis of osteoporosis. For example, as described in Ryuichiro ARAKI, Akira TAKEUCHI, et al., "Optical measurement of osteoporotic bone (1) (2)" (Abstracts at the 65th Meeting of the Japanese Society for Hygiene), a temporal waveform of light passing through an osseous tissue changed in the structure from a normal condition shows a change in a peak, a spread, a mean time delay, or the like of waveform depending upon the structural change. Explaining more specifically, the light passing through the tissue propagates therein as scattered, and thus, the frequency of chances to be scattered decreases with a coarse tissue structure so as to change the response waveform. With less scattering, the width of the waveform of output light becomes narrower, and the peak and mean time delay are shifted to the shorter time side, as compared with those of normal tissues. Accordingly, the information concerning the osteoporosis can be obtained by measuring the mean time delay of output light. In this case, the analyzing unit 50 can be set to perform an arithmetic to obtain a parameter indicating a change degree of the structure based on the mean time delay data.

The Alzheimer disease is an example in which results of changes in the scattering coefficient of the human body, the absorption coefficient thereof, the structure of tissue, and so on synthetically appear. The state and function of the patient's brain suffering from this disease are becoming uncovered to some extent by PET and MRI, and it is found that a progress of the disease results in atrophy of tissue, decrease of blood flow, and so on because of defluxion of nerve cells. By this, the light propagating in the tissue becomes less subject to light modulation due to scattering or absorption, so that the mean time delay of the output light considerably changes depending upon the degree of progress of the disease. Therefore, when the analyzing unit 50 is set so as to perform processing to obtain the degree of progress of the disease from the mean time delay data based on such a correlation, the diagnosis of the Alzheimer disease can be done by the optical measuring apparatus of the present embodiment.

The present invention is by no means limited to the above embodiments, but the invention may have various arrangements and modifications. For example, the apparatus of the present embodiment employed the single point incidence/single point detection method, but, without having to be limited to this, the apparatus may be arranged to detect photons emerging from some points of the measured object out of the probe light incident to the measured object by a plurality of photodetectors disposed around the measured object and to map the internal information of scattering medium obtained from the respective detection light. Conversely, the position of the light source may be moved for scanning to detect emerging photons by the photodetector fixed. Further, these methods can be used in combination.

Figure 5:
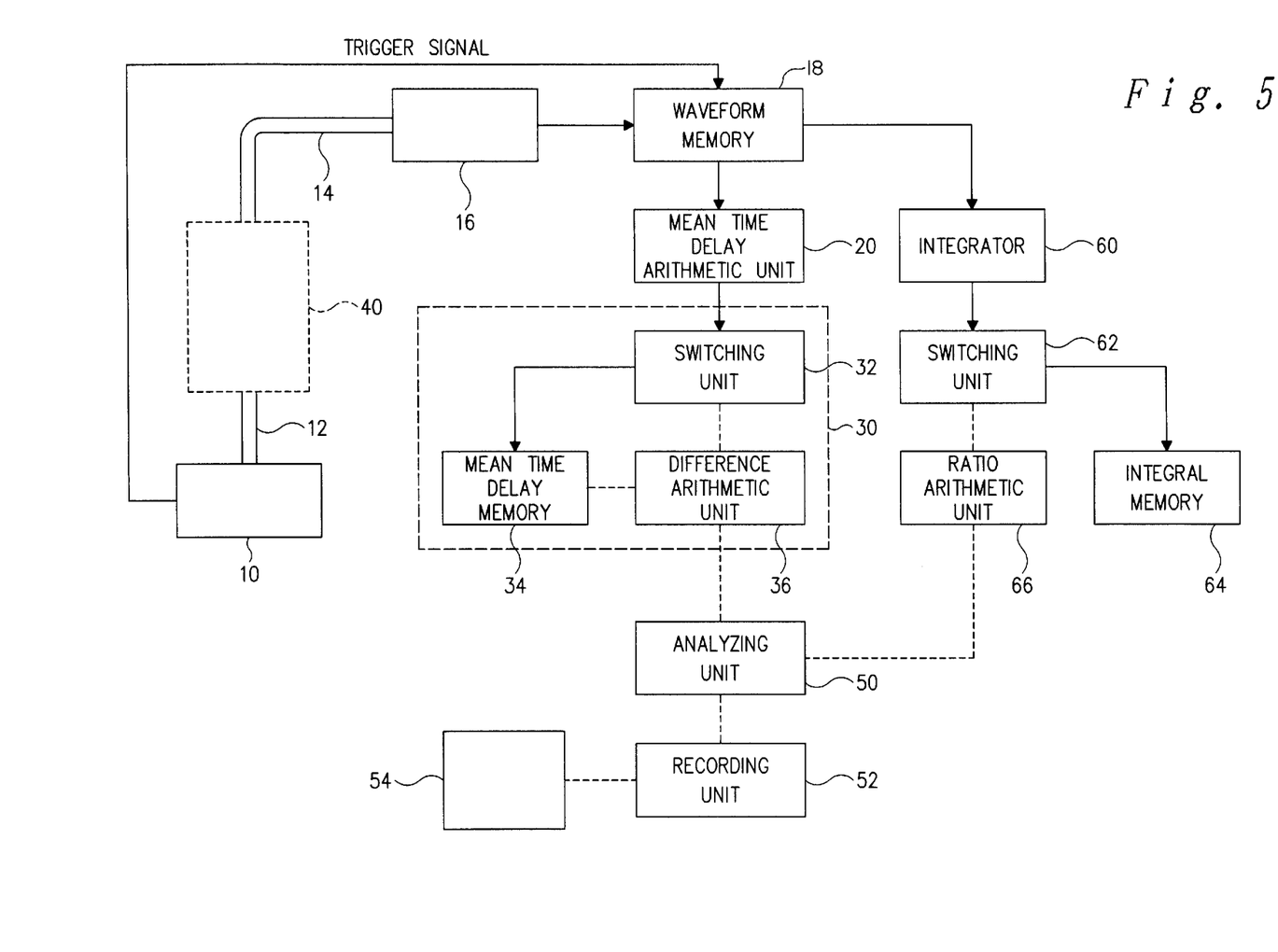
FIG. 5 is a block diagram to show another example of the optical measuring apparatus for measuring the internal information of scattering medium according to the present invention in the second state.
Figure 6:
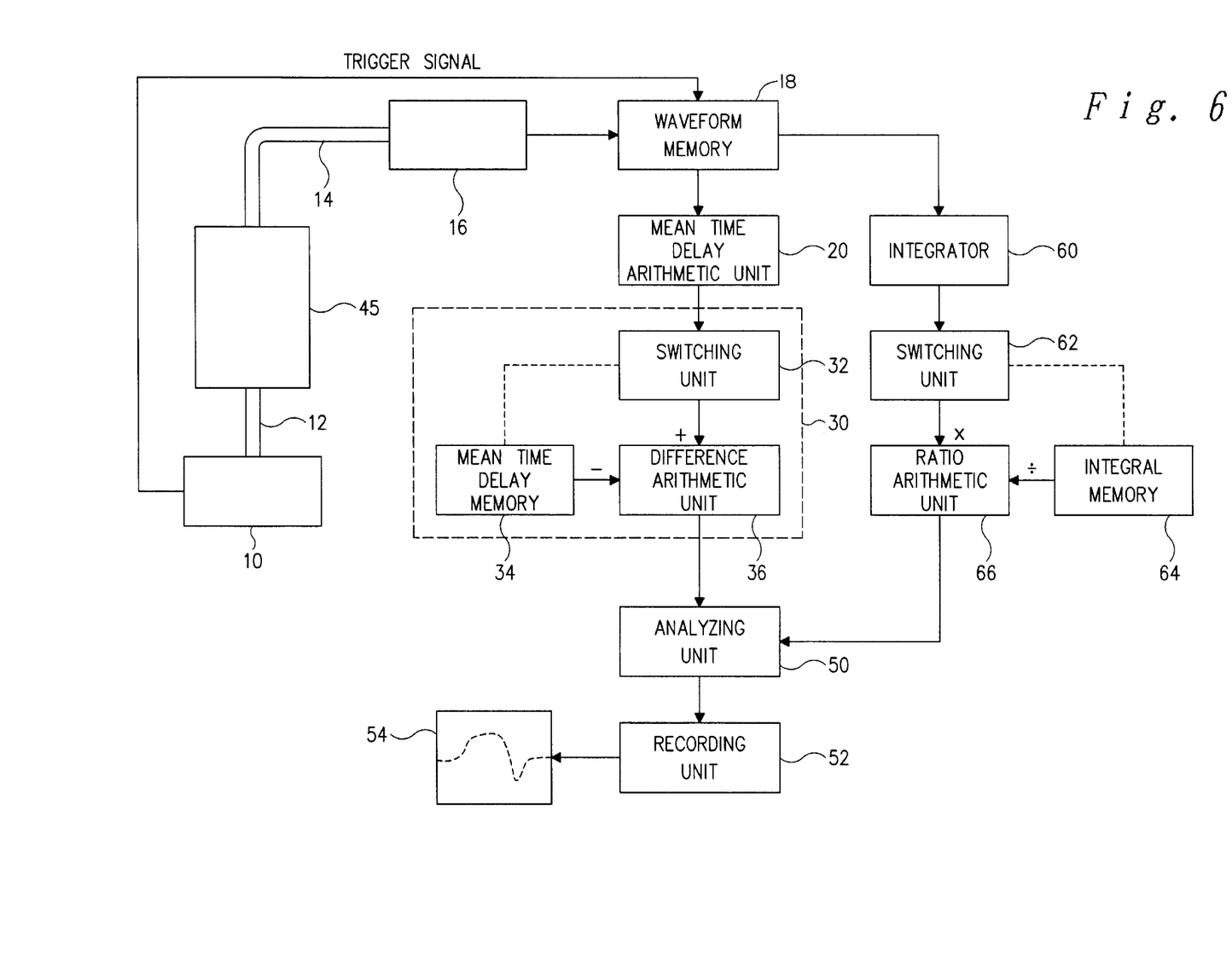
FIG. 6 is a block diagram to show the example of the optical measuring apparatus for measuring the internal information of scattering medium according to the present invention in the first state.

Next, FIG. 5 and FIG. 6 are block diagrams to show the structure and operation of a modification of the optical measuring apparatus shown in FIG. 2 and FIG. 3. In addition to the arrangement of the optical measuring apparatus shown in FIG. 2 and FIG. 3, this apparatus is further provided with an integrator 60 connected to the waveform memory 18, a switching unit 62 connected to this integrator 60, and an integral value memory 64 and a ratio arithmetic unit 66 each connected to this switching unit 62. The analyzing unit 50 is connected to the ratio arithmetic unit 66, and output data from the ratio arithmetic unit 66 is supplied to the analyzing unit 50. The recording unit 52 and displaying unit 54 are connected to the analyzing unit 50, similarly as in the apparatus shown in FIG. 2 and FIG. 3.

Next explained are the operation of the optical measuring apparatus of the present embodiment and the optical measuring method of the present embodiment.

First, as shown in FIG. 5, the light source 10 emits the probe light in the state in which the measured object is not placed in the region 40 (or in the second state), and the photodetector 16 detects the temporal waveform of the probe light having passed through the region 40. This light waveform data is taken into the waveform memory 18 at a timing synchronized with the probe light, and is stored therein.

The mean time delay arithmetic unit 20 reads the light waveform data out of the waveform memory 18 as occasion demands, and it calculates the mean time delay of the probe light based on the data. On the other hand, the integrator 60 calculates a time integration value of the probe light waveform based on the light waveform data in the waveform memory 18. The above calculation obtains the mean time delay and the integrate value of the instrumental function $h(t)$. The mean time delay data and integrate value data obtained is put into the mean time delay memory 34 and integration memory 64 through the switching units 32 and 62, respectively, and is stored therein.

Next, as shown in FIG. 6, the light source 10 emits the probe light in the state in which the measured object 45 is placed in the region 40 (or in the first state), and the photodetector 16 receives the light having passed through the measured object 45. The light waveform data detected by the photodetector 16 is stored in the waveform memory 18 and is used for the mean time delay arithmetic of the mean time delay arithmetic unit 20 and the integration arithmetic of the integrator 60. By this, the mean time delay and time integrate value of the observed waveform o(t) are calculated. The mean time delay data and integrate value data of observed waveform o(t) is supplied through the respective switching units 32 and 62 to the difference arithmetic unit 36 and to the ratio arithmetic unit 66. The difference arithmetic unit 36 reads the mean time delay data of the instrumental function h(t) out of the mean time delay memory 34 and subtracts the mean time delay of the instrumental function h(t) from the mean time delay of the observed waveform o(t) to obtain the mean time delay of the true waveform i(t). On the other hand, the ratio arithmetic unit 66 reads the integrate value data of the instrumental function h(t) out of the integration memory 64 and executes an arithmetic to divide the integrate value of the observed waveform o(t) by the integrate value of the instrumental function h(t). Arithmetic results of the difference arithmetic unit 36 and ratio arithmetic unit 66 both are sent to the analyzing unit 50.

The analyzing unit 50 performs more detailed analysis, using the mean time delay data of the true waveform i(t) and the ratio arithmetic data of integrate value of light waveform, than in the foregoing apparatus. The mean time delay data acquired by the measuring system of from the waveform memory 18 to the difference arithmetic unit 36 is subject to modification by various parameters including the scattering coefficient, the absorption coefficient, and so on, as described previously. Similarly, the integrate value of light waveform is also subject to modulation by the scattering coefficient, the absorption coefficient, and so on. Accordingly, by performing the arithmetic processing as combining the mean time delay data with the ratio arithmetic data of integrate value, contribution of scattering and contribution of absorption to the mean time delay can be readily separated from each other.

As detailed above, the optical measuring method of the present invention can quickly and easily obtain the true mean time delay of the probe light simply by subtracting the second mean time delay of the probe light detected by the light detecting means without intervention of the measured object (which is the mean time delay of the instrumental function) from the first mean time delay of the probe light transmitted or reflected by the measured object (which is the mean time delay of the observed waveform), whereby desired optical measurement can be efficiently performed within a short period of time. Since the internal information of the measured object can be acquired by analyzing the true mean time delay data of the probe light, the in vivo information can be accurately attained without cutting the organism open, for example, so that inspection or diagnosis of disease can be made within a short time period.

When the optical measuring method of the present invention is arranged to obtain the ratio of the first integral value of the waveform of the probe light transmitted or reflected by the measured object and the second integral value of the waveform of the probe light detected by the light detecting means without intervention of the measured object, it becomes possible to obtain the more detailed internal information of the measured object by analyzing the ratio and the true mean time delay data.

The optical measuring apparatus of the present invention can efficiently perform desired optical measurement within a short period of time, because the first arithmetic processing section quickly and easily obtains the true mean time delay of the probe light simply by subtracting the second mean time delay from the first mean time delay.

With the apparatus provided with the first and second light waveguide means among the optical measuring apparatus of the present invention, the first light waveguide means can easily and surely guide the probe light from the light source to the measured object while the second light waveguide means can surely guide the probe light transmitted or reflected by the measured object to the light detecting means, thereby enabling to perform the optical measurement of measured object more easily.

With the apparatus provided with the analyzing unit among the optical measuring apparatus of the present invention, the analyzing unit acquires various internal information of scattering medium by analyzing the true mean time delay data of the probe light, and, for example, the in vivo information can be accurately attained without cutting the organism open, thereby enabling to perform inspection or diagnosis of disease within a short period of time.

With the apparatus provided with the second arithmetic processing section among the optical measuring apparatus of the present invention, the second arithmetic processing section obtains the ratio of the first integral value and the second integral value and the analyzing unit analyzes the ratio arithmetic data and the true mean time delay data of probe light, whereby more detailed internal information of measured object can be attained, thereby enabling to perform inspection or diagnosis of disease more suitably.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No.218510/1995 filed on Aug. 28, 1995 is hereby incorporated by reference.

What is claimed is:

1. An optical measuring method comprising:
a first step of, in a first state in which a measured object is placed in a predetermined place, emitting probe light from a light source onto said measured object and detecting said probe light transmitted or reflected by said measured object by means of light detecting means to obtain a first mean time delay of said probe light;
a second step of, in a second state in which said measured object is not placed in said predetermined place, emitting said probe light from said light source to said predetermined place and detecting said probe light passing through said predetermined place without intervention of said measured object by said light detecting means to obtain a second mean time delay; and
a third step of subtracting said second mean time delay from said first mean time delay to obtain a true mean time delay.

2. The method according to claim 1, further comprising a fourth step of analyzing said true mean time delay obtained in said third step to obtain internal information of said measured object.

3. The method according to claim 1, further comprising:
a fifth step of, in said first state in which said measured object is placed in said predetermined place, emitting said probe light from said light source to said measured object and detecting said probe light transmitted or reflected by said measured object by said light detecting means to obtain a first integral value of a waveform of said probe light;
a sixth step of, in said second state in which said measured object is not placed in said predetermined place, emitting said probe light from said light source to said predetermined place and detecting said probe light passing through said predetermined place without intervention of said measured object by said light detecting means to obtain a second integral value of a waveform of said probe light; and a seventh step of obtaining a ratio of said first integral value and said second integral value.

4. The method according to claim 3, further comprising an eighth step of analyzing said true mean time delay obtained in said third step and the ratio of said first integral value and said second integral value obtained in said seventh step to obtain internal information of said measured object.

5. The method according to claim 1, wherein said measured object is a scattering medium and wherein said internal information is at least one information selected from the group consisting of a constant concerning absorption of said scattering medium, a constant concerning scattering thereof, a refractive index thereof, a degree of heterogeneity of composition thereof, and a constant concerning structure thereof.

6. An optical measuring apparatus comprising:

a light source for emitting probe light to be guided to a predetermined place;

light detecting means for detecting said probe light output from said predetermined place; and a first arithmetic processing portion for calculating a first mean time delay of the probe light transmitted or reflected by a measured object, based on said probe light detected by said light detecting means in a first state in which said measured object is placed in said predetermined place, calculating a second mean time delay of the probe light passing through said predetermined place without intervention of said measured object, based on said probe light detected by said light detecting means in a second state in which said measured object is not placed in said predetermined place, and subtracting said second mean time delay from said first mean time delay to obtain a true mean time delay.

7. The apparatus according to claim 6, wherein said first arithmetic processing portion comprises a mean time delay arithmetic unit for calculating a mean time delay of said probe light detected by said light detecting means to obtain said first mean time delay and said second mean time delay, and a difference arithmetic unit for subtracting said second mean time delay from said first mean time delay to obtain the true mean time delay.

8. The apparatus according to claim 7, wherein said difference arithmetic unit comprises first switching means for switching a destination of output data from said mean time delay arithmetic unit, first memory means connected to said first switching means and arranged to memorize said second mean time delay, said difference arithmetic means connected to said first switching means and to said first memory means and arranged to subtract said second mean time delay stored in said first memory means from said first mean time delay to obtain said true mean time delay.

9. The apparatus according to claim 6, further comprising first light waveguide means, one end of which is connected to said light source and the other end of which is disposed to face said predetermined place, for guiding said probe light to said predetermined place, and second light waveguide means, one end of which is connected to said light detecting means and the other end of which is disposed to face said predetermined place, for guiding said probe light output from said predetermined place to said light detecting means.

10. The apparatus according to claim 6, further comprising an analyzing unit for analyzing said true mean time delay obtained by said first arithmetic processing portion to obtain the internal information of said measured object.

11. The apparatus according to claim 10, wherein said measured object is a scattering medium and wherein said analyzing unit is arranged to execute an analysis to obtain a constant concerning absorption of said scattering medium, based on said true mean time delay obtained by said first arithmetic processing portion.

12. The apparatus according to claim 10, wherein said measured object is a scattering medium and wherein said analyzing unit is arranged to execute an analysis to obtain a constant concerning scattering of said scattering medium, based on said true mean time delay obtained by said first arithmetic processing portion.

13. The apparatus according to claim 10, wherein said measured object is a scattering medium and wherein said analyzing unit is arranged to execute an analysis to obtain a refractive index of said scattering medium, based on said true mean time delay obtained by said first arithmetic processing portion.

14. The apparatus according to claim 10, wherein said measured object is a scattering medium and wherein said analyzing unit is arranged to execute an analysis to obtain a degree of heterogeneity of composition of said scattering medium, based on said true mean time delay obtained by said first arithmetic processing portion.

15. The apparatus according to claim 10, wherein said measured object is a scattering medium and wherein said analyzing unit is arranged to execute an analysis to obtain a constant concerning structure of said scattering medium, based on said true mean time delay obtained by said first arithmetic processing portion.

16. The apparatus according to claim 10, further comprising a second arithmetic processing portion for calculating a first integral value of a waveform of said probe light transmitted or reflected by said measured object, based on the probe light detected by said light detecting means in the first state in which said measured object is placed in said predetermined place, calculating a second integral value of a waveform of said probe light passing through said predetermined place without intervention of said measured object, based on said probe light detected by said light detecting means in the second state in which said measured object is not placed in said predetermined place, and obtaining a ratio of said first integral value and said second integral value, wherein said analyzing unit is arranged to analyze said true mean time delay obtained by said first arithmetic processing portion and the ratio of said first integral value and said second integral value obtained by said second arithmetic processing portion to obtain the internal information of said measured object.

17. The apparatus according to claim 16, wherein said second arithmetic processing portion comprises an integration arithmetic unit for calculating an integral value of a waveform of said probe light detected by said light detecting means to obtain said first integral value and said second integral value, and a ratio arithmetic unit for obtaining the ratio of said first integral value and said second integral value.

18. The apparatus according to claim 17, wherein said ratio arithmetic unit comprises second switching means for switching a destination of output data from said integration arithmetic unit, second memory means connected to said second switching means and arranged to store said second integral value, and ratio arithmetic means connected to said second switching means and to said second memory means and arranged to obtain the ratio of said first integral value and said second integral value stored in said second memory means.

* * * * *

UNITED STATES PATENT AND TRADEMARK OFFICE
CERTIFICATE OF CORRECTION

PATENT NO. : 5,774,223
DATED : June 30, 1998
INVENTOR(S) : URAKAMI, et al

It is certified that error appears in the above-identified patent and that said Letters Patent is hereby corrected as shown below:

TITLE PAGE:

[73] Assignee: please change assignee's city from "Shiuoka-ken" to

--Shizuoka-ken--

Signed and Sealed this

Twenty-fourth Day of November,1998

Attest:

BRUCE LEHMAN

Attesting Officer

Commissioner of Patents and Trademarks